(12) United States Patent
Mewes et al.

(10) Patent No.: US 10,130,435 B2
(45) Date of Patent: Nov. 20, 2018

(54) OPERATING A MEDICAL-ROBOTIC DEVICE AND A MEDICAL-ROBOTIC DEVICE

(71) Applicants: Philip Mewes, Nürnberg (DE); Michael Wiets, Erlangen (DE)

(72) Inventors: Philip Mewes, Nürnberg (DE); Michael Wiets, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 71 days.

(21) Appl. No.: 14/998,133

(22) Filed: Dec. 23, 2015

(65) Prior Publication Data

US 2016/0199141 A1  Jul. 14, 2016

(30) Foreign Application Priority Data

Dec. 23, 2014  (DE) .................. 10 2014 226 899

(51) Int. Cl.
*A61B 34/32*  (2016.01)
*A61B 34/10*  (2016.01)
(Continued)

(52) U.S. Cl.
CPC .............. *A61B 34/32* (2016.02); *A61B 34/10* (2016.02); *A61B 34/30* (2016.02); *B25J 9/1656* (2013.01);
(Continued)

(58) Field of Classification Search
CPC ........... G05B 2219/37074; G05B 2219/40418; A61B 34/10; A61B 34/107;
(Continued)

(56) References Cited

U.S. PATENT DOCUMENTS 5,086,401 A * 2/1992 Glassman .............. A61B 34/20
606/53
5,279,309 A  1/1994 Taylor et al.
(Continued)

FOREIGN PATENT DOCUMENTS

CN  1481764 A   3/2004
CN  101870107 A  10/2010
(Continued)

OTHER PUBLICATIONS

German Office Action for related German Application No. 10 2014 226 899.0, dated Oct. 16, 2015, with English Translation.
(Continued)

*Primary Examiner* — Dale Moyer
(74) *Attorney, Agent, or Firm* — Lempia Summerfield Katz LLC

(57) ABSTRACT

A method for operating a medical-robotic device is provided. The robotic device includes a number of components able to be moved autonomously in an environment of the robotic device. Planning data for an autonomous movement or constraint of at least one subset of the movable components is provided to the robotic device. A movement or constraint of the corresponding movable components to be carried out autonomously by the robotic device is planned based on the planning data provided. The planned movement or constraint is visually presented. A way for an operator to exert influence on the planned movement or constraint is provided, and the movement or constraint is autonomously carried out as a function of the influence exerted.

22 Claims, 2 Drawing Sheets

(51) Int. Cl.
 A61B 34/30 (2016.01)
 B25J 9/16 (2006.01)
 A61B 5/00 (2006.01)
(52) U.S. Cl.
 CPC ........... *B25J 9/1664* (2013.01); *A61B 5/0037* (2013.01); *A61B 2034/107* (2016.02); *G05B 2219/37074* (2013.01); *G05B 2219/40091* (2013.01); *G05B 2219/40418* (2013.01); *G05B 2219/40517* (2013.01); *G05B 2219/40609* (2013.01); *G05B 2219/45123* (2013.01); *G05B 2219/45166* (2013.01)
(58) Field of Classification Search
 CPC .... A61B 2017/00022; A61B 2090/365; A61B 2034/2068; A61B 34/32; A61B 34/20; A61B 2017/00699; A61B 2017/00703
 See application file for complete search history.

(56) References Cited

U.S. PATENT DOCUMENTS

| | | | | |
|---|---|---|---|---|
| 8,812,077 B2* | 8/2014 | Dempsey | ............. | A61N 5/1045 600/410 |
| 9,668,768 B2* | 6/2017 | Piron | ................. | A61B 17/3421 |
| 2004/0024311 A1* | 2/2004 | Quaid, III | ............. | A61B 34/20 600/428 |
| 2004/0106916 A1* | 6/2004 | Quaid | .................... | A61B 34/20 606/1 |
| 2004/0128026 A1* | 7/2004 | Harris | .................... | B25J 9/1689 700/245 |
| 2005/0096892 A1 | 5/2005 | Watanabe et al. | | |
| 2007/0049861 A1 | 3/2007 | Gundel | | |
| 2009/0182224 A1* | 7/2009 | Shmarak | ................. | A61B 5/061 600/424 |
| 2011/0066282 A1 | 3/2011 | Bosscher et al. | | |
| 2012/0120091 A1 | 5/2012 | Koudijs et al. | | |
| 2012/0165652 A1* | 6/2012 | Dempsey | ............. | A61N 5/1045 600/411 |
| 2014/0276953 A1* | 9/2014 | Swarup | .................. | B25J 18/007 606/130 |
| 2015/0005785 A1* | 1/2015 | Olson | .................... | A61B 34/32 606/130 |
| 2015/0359603 A1* | 12/2015 | Levy | ...................... | A61B 34/10 703/2 |
| 2016/0022286 A1* | 1/2016 | Borries | .................. | A61B 17/15 606/87 |

FOREIGN PATENT DOCUMENTS

| | | |
|---|---|---|
| CN | 103230304 A | 8/2013 |
| CN | 103536364 A | 1/2014 |
| CN | 103961178 A | 8/2014 |
| EP | 1527850 A2 | 5/2005 |

OTHER PUBLICATIONS

Chinese Office Action for Chinese Application No. 201510977421.4, dated Apr. 28, 2018, with English translation.

* cited by examiner

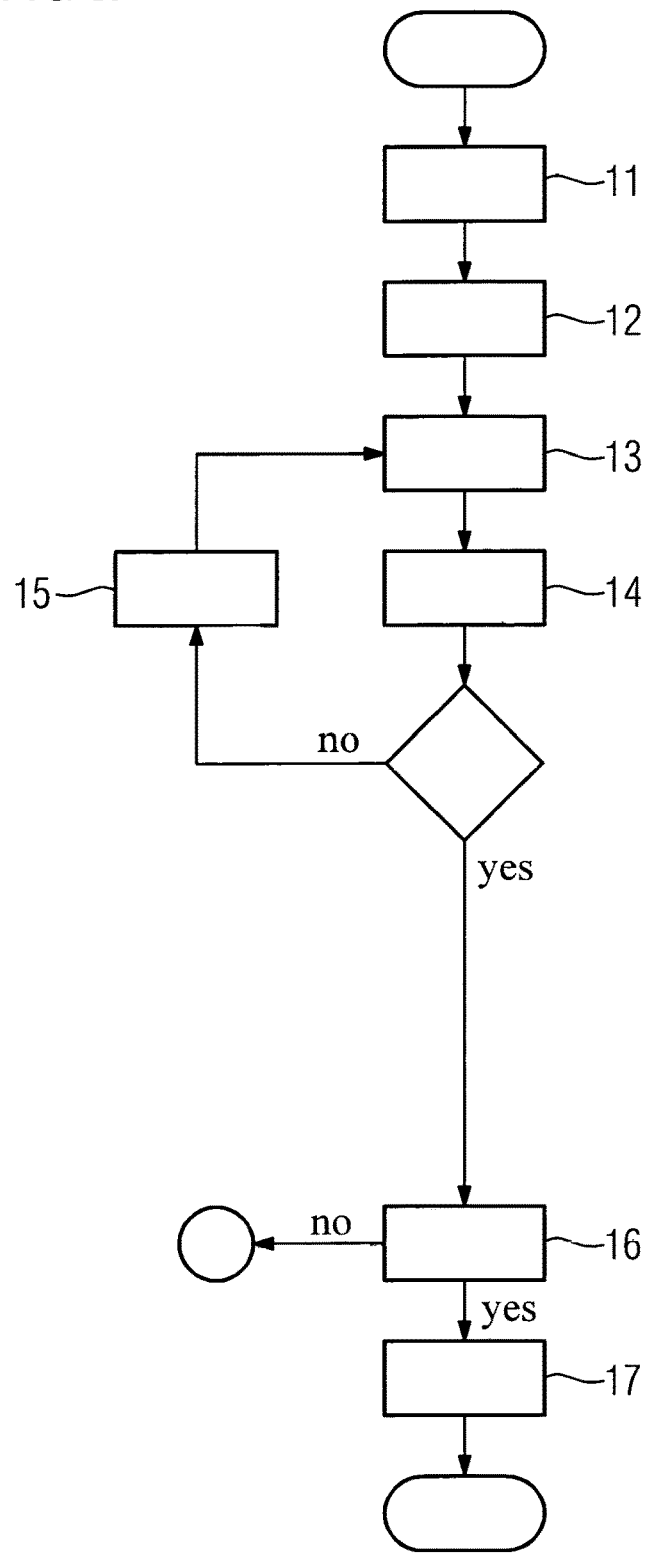

OPERATING A MEDICAL-ROBOTIC DEVICE AND A MEDICAL-ROBOTIC DEVICE

This application claims the benefit of DE 10 2014 226 899.0, filed on Dec. 23, 2014, which is hereby incorporated by reference in its entirety.

BACKGROUND

The present embodiments relate to operating a kinematically overdetermined medical-robotic device.

In a medical-robotic device that has components able to be moved in an environment of the robotic device, the topic of a danger of collision between the movable components (e.g., mechanically movable components of a kinematic chain of the robotic device, and persons (a patient) and objects in the environment) arises. This problem may be exacerbated by various factors (e.g., if the movable components are located in the immediate vicinity of a patient or are possibly introduced into a patient). Also, if the movable components are expanded by one or more medical or surgical devices, in that these devices are attached to one of the movable components, there is increased danger, since with unskilled movement, cutting tools or coagulation devices, for example, open up the possibility of injuring the patient. Unforeseen movements of a patient or operator (e.g., hospital staff) into a movement of the movable components of the medical-robotic (e.g., robotic device) exacerbates the problem of the danger of a collision.

Accordingly, known robotic systems, which are not introduced into a patient, for example, have mechanical collision detectors or perform planned movements in a safety run or mode with a reduced speed of movement of the movable components.

Known robotic systems that are introduced into the patient carry out movements in a tele-manipulation mode, providing that the movements of the movable components are always made directly by an input device (e.g., a Human-Machine Interface (HMI)). Autonomous movements are not carried out, for example, by the robotic system, so that a collision control directly by the operator is also provided. An example is, for example, the DaVinci system from Intuitiv Surgical. Other known robotic systems, which are introduced into the patient, such as the Catheter robot made by Hansen, for example, move within an enclosed anatomical space, for example, in just one dimension in a ureter.

SUMMARY AND DESCRIPTION

The scope of the present invention is defined solely by the appended claims and is not affected to any degree by the statements within this summary.

The present embodiments may obviate one or more of the drawbacks or limitations in the related art. For example, the safety of a medical-robotic device is enhanced, and a safety concept that is able to be applied to autonomously-movable or autonomously-moving components of the robotic device is realized.

A method serves to operate a kinematically overdetermined medical-robotic device that has a number of components able to be moved autonomously in an environment of the robotic device. For example, this may involve a kinematically overdetermined medical-robotic device. For example, the robotic device may have a kinematic chain of a number of movable components. A medical (e.g., surgical) device may be attached to an end element of the kinematic chain. A kinematic overdetermination allows an end point of a movement to be reached via different movement trajectories or movement paths.

The method features a series of acts. Initially, planning data for an autonomous movement or constraint of at least one subset of the movable components is provided to the robotic device. A constraint may be a constraint or prevention of a movement (e.g., of a movement made directly or indirectly by an operator). A constraint may be the establishing or maintaining of a constraint. Thus, an active constraint (e.g., an explicit limiting of a movability of the movable components) may be realized as part of an overall movement. In this case, a semi-autonomous overall movement may be supported by the method in which specific movable components are moved by an operator, and these and/or other movable components are constrained or moved autonomously.

The subset may involve a subset of the movable components that changes over time. Thus, an autonomous movement or constraint of a first subset of movable components may be followed by an autonomous movement or constraint of a second subset. In this case, the second subset may be wholly or only partly different from the first subset. The data may be provided by an operator, automatically or semi-automatically. The planning data may include a position to be reached by one of the movable components through the movement.

A subsequent act is the planning of a movement or constraint of the corresponding movable components to be carried out autonomously by the robotic device, based on the planning data provided. The corresponding movable components are, for example, the movable components of the subset for which the planning data is provided. As part of the planning, a number of movement paths or movement trajectories that, for example, fulfill the boundary conditions determined by the planning data may be evaluated. One of these movement paths is then defined as a result of the planning data for the movement or constraint of the movable components to be carried out autonomously.

This is followed by a visual presentation of the planned movement or constraint. This may be done by a display such as, for example, a screen and/or a hologram and/or a projection facility. A way (e.g., device) of enabling an operator to exert influence on the planned movement or constraint is provided in another act. This way may involve both hardware (e.g., an emergency-off button) and also software. The movement or constraint is carried out autonomously as a function of the influence exerted. Thus, the planned movement or constraint by the robotic device may be carried out by the robotic device either unchanged, changed or not at all. If the robotic device has a kinematic overdetermination, this allows a change of the movement or constraint without a predetermined target or another predetermined characteristic of the movement or constraint (e.g., a target location of one of the movable components) necessarily having to be changed.

This has the advantage that, before the actual robotic movement or constraint is carried out as a part of a medical action, this movement or constraint is displayed to the operator (e.g., as a kind of simulation), so that the operator may check the movement or constraint and ensure that a movement or constraint injuring patient or staff or movement or constraint causing material damage is not carried out by the robot. Since a way is provided allowing influence to be exerted by the operator, the operator may intervene as the operator thinks fit as soon as this is deemed necessary. It is thus also provided for a robotic device with autonomously movable components that no danger situation is caused by the autonomous carrying out of a movement or constraint, since the danger situation may be prevented a priori by influencing the action before the action is carried out. This makes a decisive contribution to enhancing safety, since previous safety mechanisms only intervene into an autonomous movement that has already taken place. This, however, because of the high speed of movement of modern robotic devices and the restricted reaction capability of an operator, establishes safety after the occurrence of a danger situation (e.g., a posteriori) and thus minimizes damage rather than preventing the damage.

There may also be provision for carrying out the movement or constraint autonomously in stages and correspondingly to plan, present and carry out the planning, presentation and provision, as well as if necessary, also to run the autonomous execution repeatedly and if necessary while doing so, to plan, present and carry out part movements or sections of constraints as part of an overall movement. This has the advantage that even a complex execution sequence is shown and executed verifiably for the operator, and the safety for the overall movement is increased precisely through the then repeated opportunities to exert influence on the planned part movements or sections of constraints.

In an embodiment, the way for influencing the planned movement or constraint is or includes a device or other way for adapting or changing an execution sequence of the planned movement or constraint. In such cases, for example, the visually presented planned movement or constraint may be changed directly in the visual presentation (e.g., by mouse clicks (drag&drop) and/or further software). This has the advantage that planned movement or constraint, which is dangerous in the estimation of the operator, for example, may be directly adapted by the operator. When the robotic device is kinematically overdetermined, a predetermined end point of a movement by the movable component may be reached in this way, for example, via a movement trajectory other than that provided for by the planned movement (e.g., via an adapted execution sequence of the planned movement). Thus, an original target of the movement and thus of the medical action, within the framework of which the movement takes place, may be achieved, and simultaneously, danger may be prevented. By contrast, a simple abortion of the movement would likewise enhance safety but would not contribute to reaching the actual target.

In an embodiment of the method, an adaptation of the execution sequence of the planned movement or constraint takes place via the provided device before the autonomous execution of the movement or constraint, as well as a visual presentation of the adapted planned movement or constraint. Thus through the adaptation of the execution sequence, the movement trajectory of the planned movement or a corresponding constraint may be changed or adapted, respectively. Accordingly, after the visual presentation of the adapted planned movement or constraint, this planned movement or constraint is carried out autonomously. There may also be a repeated adaptation of the execution sequence and a repeated visual presentation of the adapted planned movement or constraint. Accordingly, the autonomous carrying out of the last movement or constraint presented visually then takes place (e.g., the movement). The autonomous carrying out takes account of all adaptation processes. In this way, the original movement trajectory of the movable components may be replaced by a changed movement trajectory defined by the operator.

In a further embodiment, a request for a confirmation from the operator for the planned movement or constraint is provided (e.g., via the device provided) before the movement or constraint is carried out autonomously. In this case, the movement or constraint is only carried out autonomously if the confirmation is provided by the operator. The confirmation may involve both an explicit and also an implicit confirmation. An explicit confirmation may be a request for action to the operator, within the framework of which a positive or negative result is achieved for the confirmation by an operator action. An implicit confirmation may be the provision of an opportunity for a confirmation activity through an operator action by the operator, which, if it passes without being used (e.g., after a predetermined period of time), is automatically assumed to be a positive or a negative confirmation. This has the advantage that an obligatory confirmation by an operator may be realized, so that it is provided that the robotic device does not carry out an autonomous movement without supervision or unexpectedly.

In a further embodiment, the visual presentation includes a presentation of the movable components of the robotic device. In this case, the presentation may include a model-based presentation of the movable components (e.g., an animation). This has the advantage that the planned movement or constraint or the planned movement path, respectively, is intuitively visualized and is easy to verify for an operator.

In one embodiment, the visual presentation may include a presentation of the patient or an anatomical sub-area of the patient. This presentation can be based on one or more recorded images of the patient or of the anatomical sub-area. This has the advantage that the danger of the planned movement or constraint is more easily able to be estimated by the operator. A particular safety is achieved, for example, precisely in a combination with aforementioned form of embodiment, since in this way, via a visual presentation both of the patient or of the relevant (e.g., anatomical) subarea of the patient and also of the movable components, an informative simulation of the planned movement or constraint and one that is verifiable for the operator is achieved.

The recorded image may include a recorded x-ray image and/or a magnetic resonance tomography image and/or a computed tomography image and/or a positron emission tomography image. Advantageous, for example, is also an image recorded as part of a rotation angiography, as is provided by devices made by Siemens. However, images recorded by any imaging medical method are advantageous. The use of a segmented and/or image-registered recording is likewise included. This has the advantage that the patient or the anatomical sub-area of the patient may be presented very precisely, and accordingly, the simulation may be carried out precisely. Thus, an operator may recognize a possible danger situation especially well. This very much benefits from the use of segmented and/or image-registered recordings, since these are especially accurate and simple to evaluate.

In a further embodiment, a distance between one or more of the movable components or a number of distances of respective movable components may be calculated from a predetermined (e.g., visually-presented) anatomical structure of the patient for at least one part of the planned movement or constraint. In this case, the visual presentation includes a presentation of the calculated distance and/or a variable derived therefrom. The derived variable may include, for example, a maximum distance and/or a minimum distance and/or an average distance. Thus, for example, the distance or the derived variable may relate to the moveable components during the course of the movement or in the constraint. The distance or the derived variable may, for example, also relate to the distance, or the derived variable may relate to a number of distances of respective movable components to the predetermined structure in comparison to one another (e.g., in the course of the movement or in the constraint). This has the advantage that the operator is provided with additional information for assessing a danger and/or precision of the movement or constraint, so that the operator may estimate the situation especially reliably and realistically.

In this case, an acoustic and/or visual and/or haptic warning signal may be output if the distance and/or a variable derived from the distance is less than a predetermined threshold value. This has the advantage that the operator is warned about dangerous situations that are likely to occur when the movement or constraint is being carried out. The operator may react accordingly and may exert influence on the movement or constraint.

In such cases, a predetermined movement of the anatomical structure may be taken account of when calculating the distance and/or the variable derived from the distance. For example, a predetermined movement caused by a heartbeat and/or breathing may be taken into account. This is advantageous, since in this way, precisely when static information is being used (e.g., of a x-ray image or a computed tomography image or a magnetic resonance tomography image), a movement not represented in the static information and accordingly a shifting of the structurethat, if not taken into account, however, could lead to the patient being endangered may be taken into account. For example, in this way, an enlargement of the heart by the heartbeat during the assessment of the danger of a movement or constraint may also be taken into account. This is the case even if the heart currently has a smaller diameter on the visual presentation and the movement in this state of the heart would pass harmlessly over or the constraint is matched to this state of the heart In an embodiment, the visual presentation may include a display of the planned movement or constraint on the patient or the anatomical sub-area by a projection through an optical pointer. This may be done by a light beam or a laser beam. The pointer may thus mark the planned movement or constraint or the movement path by a light beam or a laser beam and may display through direct projection onto the patient's anatomy the possible presence of a collision. This brings the advantage of an external display device, such as a screen, for example, not being necessary and of an operator not having to move attention away from the patient of the anatomical sub-area, respectively. Thus, intuitive planning or checking of the planning by the operator may be provided, and also, an autonomous carrying out of a movement or constraint that takes place a number of times consecutively may be provided. The operator may remain focused on the current intervention and does not have to remove vision or possibly hands from a position or orientation advantageous for the medical procedure.

In such cases, a mechanical and/or electronic alignment of the optical pointer may be provided based on the planned movement or constraint. The alignment may also be achieved in optical ways and/or manually. This has the advantage that the planned movement is presented precisely and intuitively in dynamics or the constraint in consequences. As a result, the danger of the movement or constraint is able to be estimated especially well.

In a further embodiment, an image or a sequence of images (e.g., a film) of an environment of the movable components or one of the movable components to be obtained by an imaging instrument belonging to the robotic device is provided. The environment of the movable components may, for example, involve an environment lying inside the patient. The imaging instrument may include, for example, an endoscope or a laparoscope. In this case, the visual presentation involves an overlaying of the image obtained or of the sequence of images obtained with a presentation of the planned movement or constraint. This may take place in real time, so that the environment is presented visually as augmented reality. This is practical for an operator, since in this way, the planned movement or constraint and the environment are directly and immediately related to one another. As a consequence, the danger of the movement or constraint carried out autonomously is easy to estimate.

One or more of the present embodiments also relate to a medical-robotic device that is, for example, kinematically overdetermined and has a number of components able to be moved autonomously in an environment of the robotic device. The robotic device is configured, for at least a part of the movable components, based on the planning data provided, autonomously to plan a movement or constraint and autonomously to move or to constrain the movable components. The robotic device is further configured, before carrying out an autonomous movement or constraint of the movable components, to present the planned movement or constraint visually and to provide a way for an operator to exert influence on the planned movement or constraint.

In one embodiment, the medical-robotic device may be put into an operating mode in which the visual presentation of the planned movement or constraint and the provision of a way for the operator to exert influence on the planned movement or constraint is done before any autonomous carrying out of a movement or constraint of the movable components. This has the advantage that, for example, within the framework of a medical procedure, the safety of the robotic device may be enhanced by the operating mode being activated. This is done, for example, after a patient has arrived in the environment of the medical-robotic device. At the same time, in another further operating mode, for example, for a stowing away or cleaning of the medical-robotic device, the visual presentation and the provision of a way for exerting influence before a movement or constraint is carried out by the medical-robotic device may practically be dispensed with.

The advantages and advantageous forms of embodiment of the method for operating a medical-robotic device also apply correspondingly to the medical-robotic device and vice versa.

All features and combinations of features given in the description, as well as the features and combinations of features shown below in the figure description and/or in the figure, are not only able to be used in the combination specified in each case, but also in other combinations and also on their own without departing from the scope of the invention. Thus, versions of the invention that are not explicitly shown and explained in the figures, but are derived from and able to be created by combinations of features from the versions explained, are also to be seen as included and disclosed.

BRIEF DESCRIPTION OF THE DRAWINGS

FIG. 2 shows a schematic flow diagram of one embodiment of a method.

DETAILED DESCRIPTION

Figure 1:
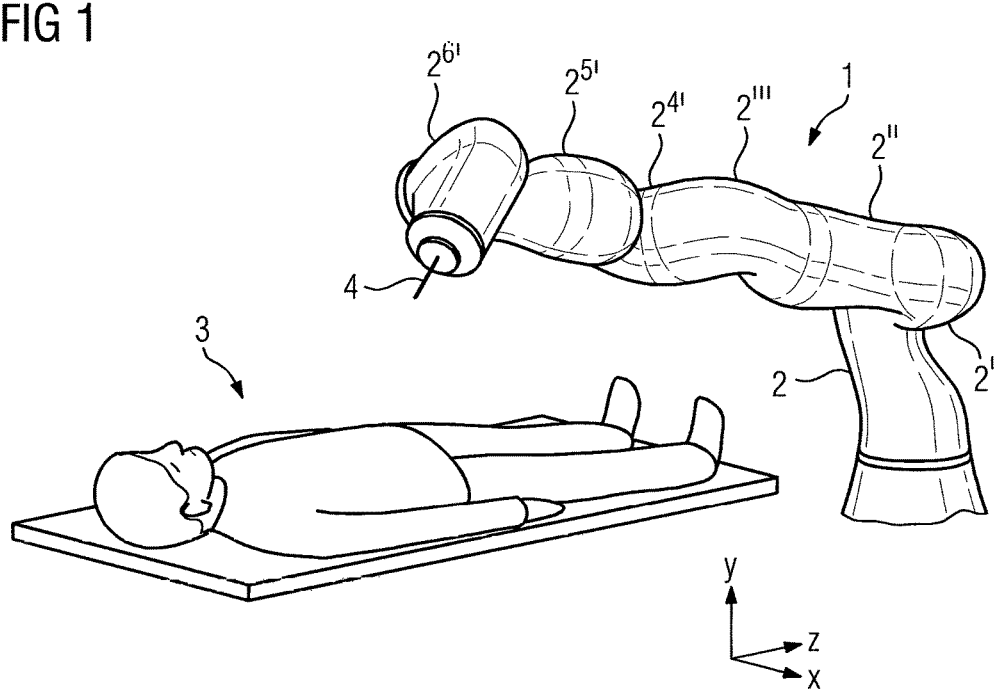
FIG. 1 shows the content of an exemplary visual presentation of the movable components of the robotic device and of a patient.

FIG. 1 is a schematic diagram of the content of a typical visual presentation of a planned movement, as may be displayed on a monitor, for example, within the framework of an exemplary form of an embodiment of a method. The content includes, for example, a model-based presentation of a robotic device 1 with movable components 2 to $2^{6'}$. In the present case, the movable components 2 to $2^{6'}$ form a kinematic chain of the robotic device 1, which may be moved autonomously by the robotic device 1. Disposed on an end element of the kinematic chain is, for example, a medical device 4 embodied as a surgical device. The medical device 4 may also be a part of the kinematic chain.

The content in the present case also includes a modeled presentation of a patient 3. In one form of embodiment of the method, the movable components 2 to $2^{6'}$ shown are moved in the presentation in accordance with the planned movement in the three spatial directions x, y, z. Thus, a three-dimensional animation or animation with a three-dimensional effect of the planned movement is previewed to the operator. Since both the robotic device and also the patient 3 may be presented visually, an operator may accordingly estimate a danger of the movement of the movable components 2 to $2^{6'}$. For example, getting too close to sensitive sub-areas of the patient may be recognized in this way.

The presentation in the present case includes a model-based exterior view of the patient 3. Movements within the patient 3 may also be planned and visually presented via an interior view. In such cases, the presentation of an interior view may also be based on a model, but may be based on suitable recorded images of the patient 3 or the corresponding sub-area of the patient 3. X-ray or MRT images are suitable, for example.

FIG. 2 shows a schematic execution sequence of one embodiment of a method for operating a kinematically overdetermined medical robotic device. The first act is the provision 11 of planning data for an autonomous movement of the movable components to the robotic device 1 (FIG. 1). The second act is planning 12 of a movement of the movable components 2 to $2^{6'}$ (FIG. 1) to be carried out based on the planning data provided by the robotic device 1 (FIG. 1). The third act is a visual presentation 13 of the planned movement. This may be done, for example, on a monitor or via a projection of the planned movement onto the patient 3 (FIG. 1) or onto an anatomical sub-area of the patient. The visual presentation 13 may also include both of the measures.

The visual presentation 13 is followed, for example, by a provision 14 of a way for the operator to exert influence on the planned movement. For example, there may be an adaptation 15 of the sequence of the planned movement on the monitor via an interaction of an operator. If the operator decides that the planned movement does not satisfy requirements, the adaptation 15 is done as the next act of the method. In this case, there is accordingly a new visual presentation 13, then the adapted planned movement. If, for example, this still does not satisfy the ideas of the operator, then in the example shown, the adaptation 15 and the visual presentation 13 are repeated until the operator 15 no longer deems any adaptation to be necessary. In the form of embodiment shown, for safety reasons, after the provision 14 and before an autonomous carrying out 17, there is always a request 16 for a confirmation from the operator for the planned movement. The operator thus has the opportunity of making a final check and has the responsibility in practice for the autonomous carrying out 17 of the movement taking place after the request 16 for the confirmation. If no confirmation is received, the method is ended without the carrying out 17 of the movement. As an alternative, the planning 12 may be carried out once again. Thus, only when the operator gives a positive confirmation does the autonomous carrying out 17 of the movement actually take place.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for operating a medical-robotic device, wherein the medical-robotic device includes a number of components that are moveable autonomously in an environment of the medical-robotic device, the method comprising:
providing planning data for a constraint of at least one subset of the movable components to the medical-robotic device;
planning a movement of the corresponding movable components to be carried out autonomously by the medical-robotic device based on the planning data provided including the constraint;
visually presenting the planned movement or the constraint;
providing an input allowing an operator to exert influence on the planned movement or the constraint;
autonomously carrying out the movement as a function of the influence exerted.

2. The method of claim 1, wherein the input is configured to adapt an execution sequence of the planned movement or the constraint.

3. The method of claim 2, further comprising:
adapting the execution sequence of the planned movement or the constraint via the input before the autonomous carrying out of the movement; and
visually presenting the adapted planned movement or the constraint.

4. The method of claim 1, further comprising:
requesting a confirmation from the operator for the planned movement or the constraint via the input before the autonomous carrying out of the movement,
wherein the autonomous carrying out is only done if the confirmation is provided by the operator.

5. The method of claim 1, wherein the visual presentation comprises a presentation of the movable components of the medical-robotic device.

6. The method of claim 1, wherein the visual presentation comprises a presentation of a patient or of an anatomical sub-area of the patient.

7. The method of claim 6, wherein the presentation of the patient or of the anatomical sub-area of the patient is based on one or more recorded images of the patient or of the anatomical sub-area.

8. The method of claim 7, wherein the one or more recorded images comprise an x-ray image, a magnetic resonance tomography image, a computed tomography image, a positron emission tomography image, a segmented recorded image, an image-registered recorded image, or any combination thereof.

9. The method of claim 6, further comprising:
calculating a distance of a movable component from a predetermined anatomical structure of the patient for at least a part of the planned movement,
wherein the visual presentation comprises a presentation of the calculated distance, a variable derived from the calculated distance, or a combination thereof.

10. The method of claim 9, wherein the variable derived from the calculated distance comprises a maximum distance, a minimum distance, an average distance, or any combination thereof.

11. The method of claim 9, further comprising outputting an acoustic warning signal, a visual warning signal, a haptic warning signal, or any combination thereof when the distance, the variable derived from the distance, or a combination thereof is less than a predetermined threshold value.

12. The method of claim 9, further comprising taking account of a predetermined movement of the anatomical structure during the calculation of the distance, the variable derived from the distance, or a combination thereof.

13. The method of claim 12, wherein the predetermined movement of the anatomical structure comprises a movement caused by a heartbeat or by breathing.

14. The method of claim 1, wherein visually presenting the planned movement or constraint comprises displaying the planned movement or the constraint on the patient or on the anatomical sub-area of the patient by a projection by an optical pointer.

15. The method of claim 14, wherein the optical pointer comprises a light beam or a laser beam.

16. The method of claim 14, further comprising mechanically, electronically, or mechanically and electronically aligning the optical pointer based on the planned movement or the constraint.

17. The method of claim 1, further comprising obtaining an image or a sequence of images of an environment of the movable components by an imaging instrument belonging to the medical-robotic device,
wherein visually presenting the planned movement or the constraint comprises overlaying the image obtained or the image sequence obtained with a presentation of the planned movement or constraint.

18. The method of claim 17, wherein the image or sequence of images comprises a film, and
wherein the medical-robotic device comprises an endoscope or a laparoscope.

19. The method of claim 1, wherein the planning data further comprises data for a movement of at least one subset of the movable components to the medical-robotic device.

20. The method of claim 1, wherein the constraint is a limit on a mobility of at least one subset of the movable components to the medical-robotic device.

21. A medical-robotic device comprising:
a number of components moveable autonomously in an environment of the medical-robotic device,
wherein the medical-robotic device is configured, for at least a subset of the movable components based on the planning data provided, autonomously to plan a movement based on a constraint of the movement and to move the corresponding movable components, and
wherein the medical-robotic device is also configured, before the carrying out of an autonomous movement of the corresponding movable components, to visually present the planned movement or the constraint and to provide an input for the operator to exert influence on the planned movement or the constraint.

22. The medical-robotic device of claim 21, wherein the medical-robotic device is operable in an operating mode in which the visual presentation of the planned movement or the constraint and the provision of the input are done before any autonomous carrying out of a movement of the corresponding movable components.

* * * * *